(12) United States Patent
Liu et al.

(10) Patent No.: US 9,833,403 B2
(45) Date of Patent: Dec. 5, 2017

(54) NANOPARTICLES AND NANOEMULSIONS (71) Applicants: Huiwen Liu, Brighton, MA (US); Boke Zhang, Brighton, MA (US)

(72) Inventors: Huiwen Liu, Brighton, MA (US); Boke Zhang, Brighton, MA (US)

(73) Assignees: Huiwen Liu, Brighton, MA (US); Boke Zhang, Brighton, MA (US)

( * ) Notice: Subject to any disclaimer, the term of this patent is extended or adjusted under 35 U.S.C. 154(b) by 0 days.

(21) Appl. No.: 14/893,123

(22) PCT Filed: Dec. 31, 2013

(86) PCT No.: PCT/US2013/078405
§ 371 (c)(1),
(2) Date: Nov. 23, 2015

(87) PCT Pub. No.: WO2014/197008
PCT Pub. Date: Dec. 11, 2014

(65) Prior Publication Data
US 2016/0120794 A1 May 5, 2016

Related U.S. Application Data (60) Provisional application No. 61/830,335, filed on Jun. 3, 2013.

(51) Int. Cl.
| | | |
|---|---|---|
| A61K 8/97 | (2017.01) | |
| A61K 9/113 | (2006.01) | |
| A61K 9/00 | (2006.01) | |
| A61K 9/107 | (2006.01) | |
| A61K 8/49 | (2006.01) | |
| A61K 8/64 | (2006.01) | |
| A61K 8/67 | (2006.01) | |
| A61K 8/73 | (2006.01) | |
| A61Q 19/08 | (2006.01) | |
| A61K 8/06 | (2006.01) | |
| A61K 38/00 | (2006.01) | |
| B82Y 5/00 | (2011.01) | |

(52) U.S. Cl.
CPC ............... *A61K 8/97* (2013.01); *A61K 8/066* (2013.01); *A61K 8/4946* (2013.01); *A61K 8/64* (2013.01); *A61K 8/675* (2013.01); *A61K 8/735* (2013.01); *A61K 9/0014* (2013.01); *A61K 9/1075* (2013.01); *A61K 9/113* (2013.01); *A61Q 19/08* (2013.01); *A61K 38/00* (2013.01); *A61K 2800/21* (2013.01); *B82Y 5/00* (2013.01)

(58) Field of Classification Search
CPC ...... A61K 8/066; A61K 9/1075; A61K 9/113; B82Y 5/00
See application file for complete search history.

(56) References Cited

U.S. PATENT DOCUMENTS

| | | | | |
|---|---|---|---|---|
| 2009/0247635 A1* | 10/2009 | Ehrenpreis | ........... | A61K 31/197 514/561 |
| 2013/0017239 A1* | 1/2013 | Viladot Petit | ........ | A61K 8/0283 424/401 |

OTHER PUBLICATIONS

Tegeli, V.S. et al. "Pemulen as a Versatile Emulsifier" International Journal of Drug Formulation & Research Jan.-Feb. 2011, vol. 2 (1), 52-63.*

* cited by examiner

*Primary Examiner* — Timothy P Thomas
*Assistant Examiner* — Andrew S Rosenthal
(74) *Attorney, Agent, or Firm* — Anova Law Group, PLLC (57) ABSTRACT

The invention described herein is related to the preparation and usage of nanoemulsions and nanoparticles which containing biological active ingredients including cosmetic, medical and pharmaceutical active ingredients to pass skin barriers and promote cell growth with evident clinical effects. Also, the present invention contains a cosmetic formulation that can be used for skin rejuvenation, wrinkle removal, scar treatment and wounds healing.

15 Claims, 11 Drawing Sheets

NANOPARTICLES AND NANOEMULSIONS

REFERENCE TO RELATED APPLICATION

This US application claims the benefit of the filing date of U.S. Provisional Application Ser. No. 61/830,335 filed on Jun. 3, 2013, and the benefit of filing date of PCT application No. PCT/US2013/078405 filed on Dec. 31, 2013, both entitled "Compounds Encapsulated Nanoparticles and Nanoemulsions Preparation and Use Thereof". The teachings of the entire referenced applications are incorporated herein by reference.

TECHNICAL FIELD OF THE INVENTION

This invention relates generally to the preparation and usage of nanoemulsions and nanoparticles which containing biological active ingredients including cosmetic, medical and pharmaceutical active ingredients to pass skin barriers and promote cell growth with evident clinical effects.

BACKGROUND ART OF THE INVENTION

Nano material refers to the manipulation of matter on atom or molecular scale. One nanometer (nm) is one billionth, or $10^{-9}$, of a meter. By comparison, typical carbon-carbon bond lengths, or the spacing between these atoms in a molecule, are in the range 0.12-0.15 nm, and a DNA double-helix has a diameter around 2 nm. The definition used by the National Nanotechnology Initiative in the US, nano is a matter in the scale range of 1 to 100 nm [1]. Nano-particles are effectively a bridge between bulk materials and atomic or molecular structures. A bulk material should have constant physical properties regardless of its size, but at the nano-scale their properties becomes size-dependent. Nano-particles (nanoparticles and nano-particles are exchangeable in this invention) can strongly influence the mechanical properties of the material, like stiffness, elasticity, optical transparency, diffusive transport and shelf life stability [2]. Therefore they are very important for pharmaceutical, medical, food and personal care products.

In general terminology, researchers define nano-emulsions (nanoemulsions and nano-emulsions are exchangeable in this invention) as disruptions of nano-scale droplets formed by sheer-induced rupturing; micro-emulsions are usually formed by self-assembly. The micro-emulsions can also be formed with particle sizes smaller than 100 nm, spontaneous emulsification through the addition of a surfactant without a sheer usually related to the formation of equilibrium lyotropic of crystalline phases, in which the surface tension effectively vanishes and the droplets are formed by thermodynamic molecular self-assembly from the 'bottom up' [3].

As long as the particle size or matter is in nano scale, it can be called nano-emulsion (nanoemulsion) and nano-particle (nanoparticle). The micro-emulsion is in between nano-emulsion, mini-emulsion and emulsion. The micro-emulsion particle size can range from 20 nm to 200 nm or even larger.

Over the decades large molecules including biologically active compounds can only be effectively delivered across skin barriers via invasive methods such as needle injections. But this invasive method has obvious shortages due to safety issues and patient noncompliance issues such as pains. In addition to the safety concern and patient non-compliance issues from the invasive trans-dermal delivery methods, the demand for non-invasive trans-dermal delivery method has been increased more now than ever before due to more rapidly growing biotechnology derived molecules having much better therapeutic and/or cosmeceutical values than current therapies can provide. As can be expected, the non-invasive trans-dermal delivery technology of bio-active ingredients becomes very attractive and important in pharmaceutical industry as well as in cosmetics industry for better patient and consumer compliance. Unfortunately, to date there has been no suitable delivery method to meet this ever-increasing need for many obvious reasons. There have been at least two major obstacles: $1^{st}$ one is that biologically active molecules are very sensitive to the environment during the manufacturing process, storage, transportation and application processes. Changes in temperature, pH, vibrations, light, ionic strength and other additives can easily denature or destroy its biological activity. Therefore the manufacturing process and other processes involving these molecules have to be very mild and gentle, the biological activity has to be maintained throughout the entire process; $2^{nd}$ one is that the bio-molecules are large in size and difficult to get across the skin through its natural barriers. To overcome these and other practical obstacles, the delivery method has to possess the ability to enable large molecules to be delivered across each skin barrier (stratum corneum, epidermis and dermis), and the ability to maintain the biological activity throughout the whole delivering process.

With these two major requirements in place and other considerations for different bio-molecules, it's no wonder that there has been no suitable non-invasive trans-dermal method available to serve the purpose. Liposome technology has been used widely in the injectable pharmaceutical product to increase the drug active aqueous solubility and/or to have drug sustained-release characteristics such as Doxil [4, 5, 6, 7, and 8]. However, due to the higher than room temperature glass transition temperature (Tg) of phosphocholine lipids (PCs) and other lipids used in the liposome manufacturing technology, many bio-molecules cannot survive the higher temperature (i.e.: >50° C.) manufacturing process or the roughness of extrusion type processes [9]. Other micro-wounding methods such as micro-array (micro-needles) are used in cosmetics industry [10], but safety is still a major concern due to skin micro-wounds by itself and it cannot be easily operated.

Generally speaking human skin is about 250 um or less in thickness and its thickness varies in different skin sites for an individual. Human skin consists of top layer of stratum corneum, middle layer of epidermis, and lower layer of dermis where nerve terminals and cells are largely resided and abundant. Trans-dermal delivery pathways are considered to involve hair follicular channels, inter-cellular space, and intra-cellular space with the first two as the main routes [11]. As can be imagined, particle size and properties can also play important roles in the delivery of small and large molecules. Given its very small size and unique properties, nanoparticle can be a good candidate for such delicate process in trans-dermal delivery. The skin surface and the underneath are lipophilic and hydrophilic in nature, respectively. The inner skin layers and cells also have lipophilic in the cell membrane and hydrophilic inside the cells. To cross these multiple layers of skin and cells through lipophilic and hydrophilic membranes more than once, it would be very difficult for simple and single layer nanoparticle to accomplish this delicate task.

Therefore, multi-layer nanoparticles and nanoemulsions (smaller nanoparticles inside larger nanoparticles) encapsulated with active ingredients are selected, carefully designed and developed to serve this purpose. The main objective for these encapsulated multi-layer nanoparticles and nanoemulsions is to cross the skin layers without use of needles, and to deliver encapsulated contents into inner layers of skin during and after the penetration process by itself. Thus, many of experiments within this invention have been carried out to develop these multi-layer nanoparticles and nanoemulsions in very mild and gentle conditions with good stability, in an effort to encapsulate active ingredients, maintain their bio-activities and to overcome barriers from the multi-layer skin membranes of lipophilic and hydrophilic in nature.

DISCLOSURE OF THE INVENTION

A multi-layer nanoemulsion is provided herein containing two to five layers of nanoparticles in which the core particles are water-in-oil nanoparticles embedded in the oil-in-water nanoparticles. The multi-layer nanoparticles are wrapped up in a cream to form stable nanoemulsions. The water-in-oil nanoparticles have particle size less than 30 nm or less than 20 nm or less than 10 nm or less than 5 nm. The oil-in-water particles have particle size less than 80 nm or less than 50 nm or less than 40 nm or less than 30 nm. The nanoemulsions have particle size less than 150 nm or less than 100 nm or less than 80 nm or less than 60 nm or less than 50 nm or less than 30 nm. Lipophilic or hydrophobic ingredients and hydrophilic ingredients are encapsulated inside the nanoparticles or between the layers of nanoparticles or on the surface of nanoparticles or on the surface of the nanoemulsions.

The nanoparticles and nanoemulsions contain active ingredients for topical applications.

The nanoparticles and nanoemulsions contain cosmetic and cosmeceutical ingredients for cosmetic applications.

The nanoparticles and nanoemulsions contain pharmaceutical and nutraceutical ingredients for therapeutic applications.

The active ingredients contained in the multi-layer nanoparticles and nanoemulsions are selected from Palmitoyl pentapeptide KTTKS, Palmitoyl tetrapeptide GQPR, Palmitoyl GHK, other pamitoyl-oligopeptides, Hexapeptide argireline, Snap-8 octapeptide (or acetyl octapeptide-3), other oligpeptides, hyaluronic acid, allantoin, niacinamide, aloe vera, Cu-GHK tripeptide, and di-peptides.

The hyaluronic acid is encapsulated in aqueous phase with concentration range from 0.01% to 10%, and preferred range is from 0.1% to 2.0%.

The nanoparticles and nanoemulsions contain active ingredients selected from aloe vera, allantoin, niacinamide, Q10, resveratrol, vitamin C, vitamin D, vitamin E, hexapeptide argireline, octa-peptide Snap-8 (or acetyl octapeptide-3), oligo-peptides, palmitoyl-GHK, palmitoyl-KTTKS, palmitoyl-GQPR, palmitoyl-oligopeptides, stem cells, stem cell matrix, stem cell growth factors, plant stem cell growth factors, human stem cell growth factors, insulin, cell growth factors, epidermal cell growth factors (EGFs), fibroblast cell growth factors (FGFs), keratiocyte growth factors (KGFs), 5-floro-uracil, diacarbazine, celecoxib, rofecoxib, silver ions (Ag+) such as AgNO3, ibuprofen, minocycline, tetracycline, doxycycline, oxytetracycline, estriol, estradiol, progesterone.

The nanoparticles and nanoemulsions have topical applications with anti-wrinkle or wrinkle-reducing, anti-ageing, and skin firming effect, wherein Palmitoyl pentapeptide KTTKS, Palmitoyl tetrapeptide GQPR, Palmitoyl GHK, and other pamitoyl-oligopeptides are in the oil and surfactant phase, wherein Hexapeptide argireline, Snap-8 octapeptide, other oligpeptides, hyaluronic acid, allantoin, niacinamide, and aloe vera in the aqueous phase.

The nanoparticles and nanoemulsions have topical applications with skin-whitening or skin pigmentation-reducing, anti-ageing, and skin firming effect, wherein Palmitoyl GHK and other oligopeptides in the oil and surfactant phase, wherein Cu-GHK tripeptide, di-peptides, other oligopeptides, hyaluronic acid, allantoin, niacinamide, and aloe vera in the aqueous phase.

The nanoparticles and nanoemulsions have topical applications with anti-inflammatory and speedy skin wounds healing effect, wherein Palmitoyl GHK in the oil and surfactant phase, wherein Cu-GHK tripeptide, di-peptides, hyaluronic acid, allantoin, niacinamide, and aloe vera in the aqueous phase.

A method to make the multi-layer The nanoparticles and nanoemulsions, are manufactured according to comprising the following steps: 1) make smaller nanoparticles in a water-in-oil system by adding aqueous phase into a stirring oil and surfactant phase; 2) the resulting nanoparticles are then added into a stirring aqueous phase and are wrapped in an oil-in-water system to form new nanoparticles; 3) then a cream such as Pemulen is added into the newly formed nanoparticles with stirring, which are further wrapped in a cream to produce the final multi-layer nanoparticles and nanoemulsions, wherein magnetic stirring or mechanical stirring is employed during these processes for well mixing, wherein the stirring rate ranges from 10 to 5,000 rpm, preferably from 300 to 2,000 rpm, wherein the temperature of these mixing processes ranges from 5° C. to 95° C., preferably from 10° C. to 70° C.

The oil is selected from octanoic acid decanoic acid ester of glycerol, Labrafac Lipophile WL1349 oil (or capric and caprylic acid triglycerides), soybean oil, tea oil, sunflower seed oil, vegetable oil, fish oil, seasme oil, animal lipid oil, Vitamin E; wherein the surfactant is selected from Cremophor, Cremophor-EL (or macrogol-35-glycerol-rizinoleat), Cremophor EL-35, polysorbate-20 (Tween-20), polysorbate-60 (Tween-60), polysorbate-80 (Tween-80), Span-40 (or sorbitane monopalmitate), PEG.

The surfactant used to make nanoparticles and nanoemulsions is a single-surfactant system or two-surfactant system or more than two-surfactant system.

The weight ratio of the oil and surfactant phase to the aqueous phase is from 1:99 to 40:60, preferably from 5:95 to 20:80.

The weight ratio of the surfactant to the oil of the oil and surfactant phase is from 10:1 to 1:10, preferably from 3:1 to 1:3.

The cream is selected from Pemulen TR1, Pemulen TR2, Carbomer, PCCA vanishing cream, or any cream that can form an emulsion with the nanoparticles.

The cream is prepared from the following steps: Phase 1, purified water (135 g), methyparaben (0.4 g), glycerin (3 g) and phenoxyethenol (6.0 g) are mixed well in a beaker at 70° C.; Phase 2, mineral oil (5 g), avocado oil (5 g), isopropyl myristate (5 g), white petrolatum (4 g), vitamin E (4.6 g), emulsifying wax (18 g), bees wax (7 g), cetearyl alcohol (3 g), ethylhexylglycerin (2 g) and propylparaben are heated to 70° C., melted and mixed well in a separate container; Transfer Phase 2 at 70° C. into Phase 1 and mix well at 70° C., stir and cool to room temperature, wherein total 200 gram cream is prepared from the above steps.

Figure 1:
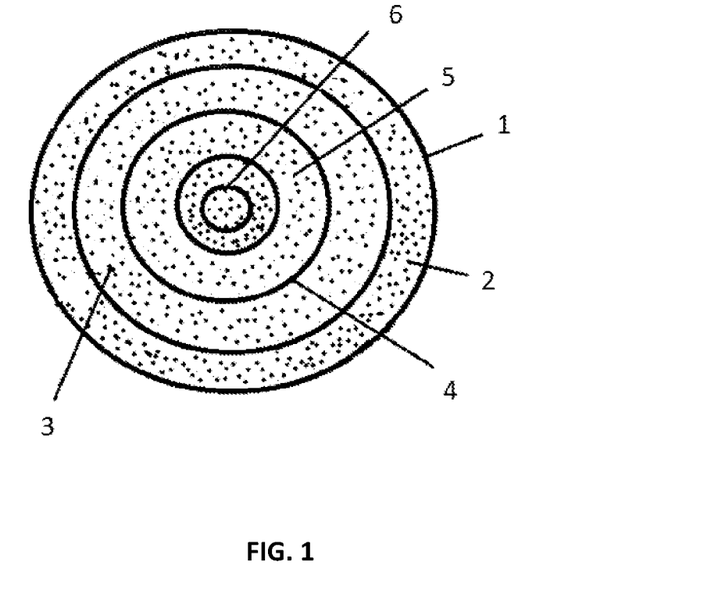
Figure 2A:
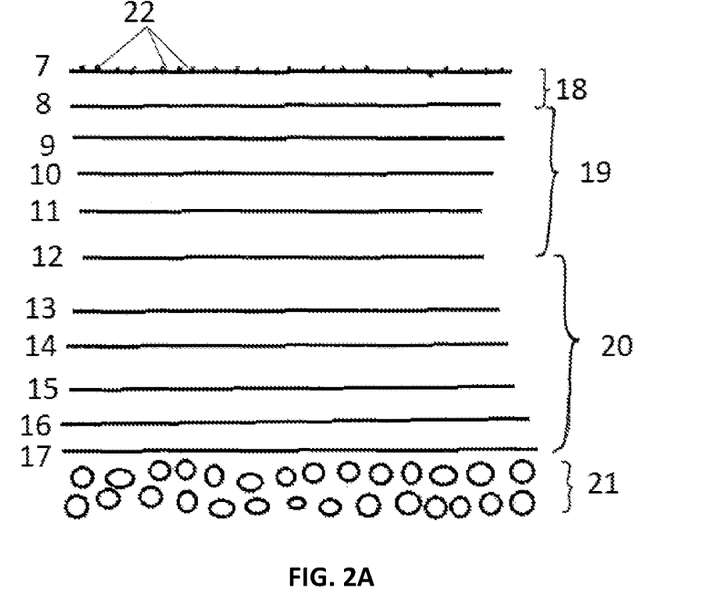
Figure 2B:
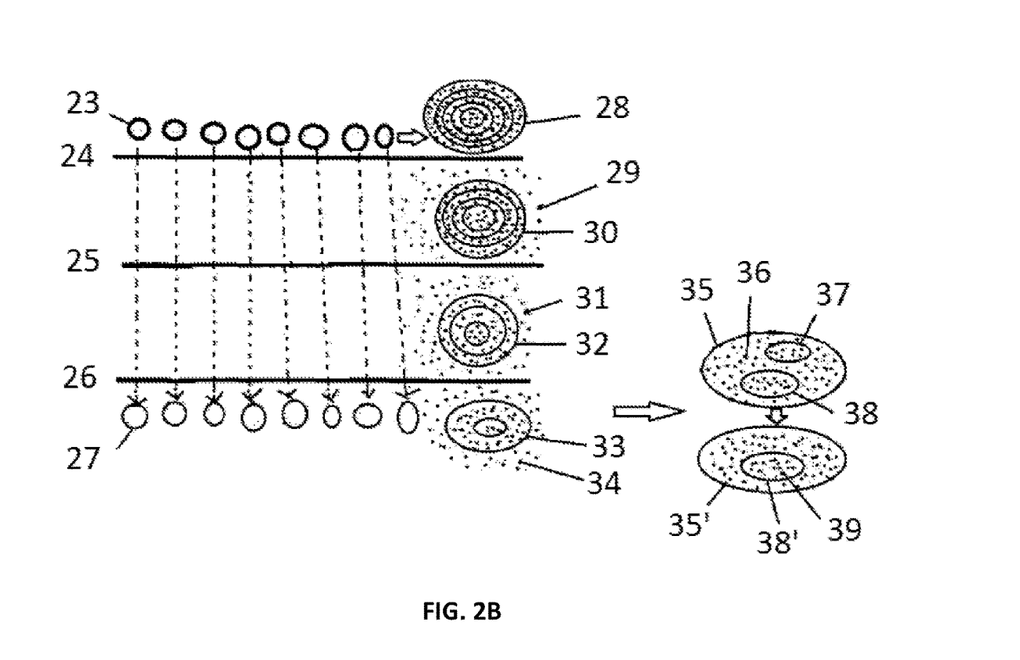
Figure 3:
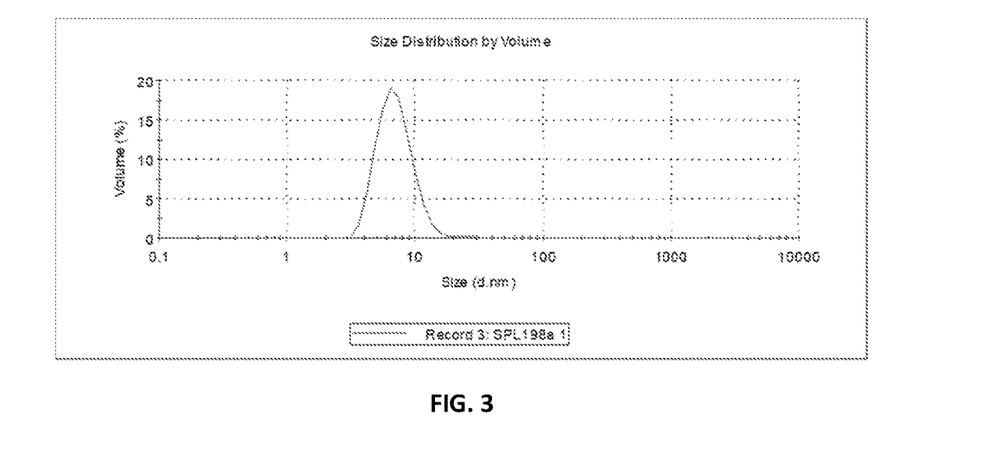
Figure 4:
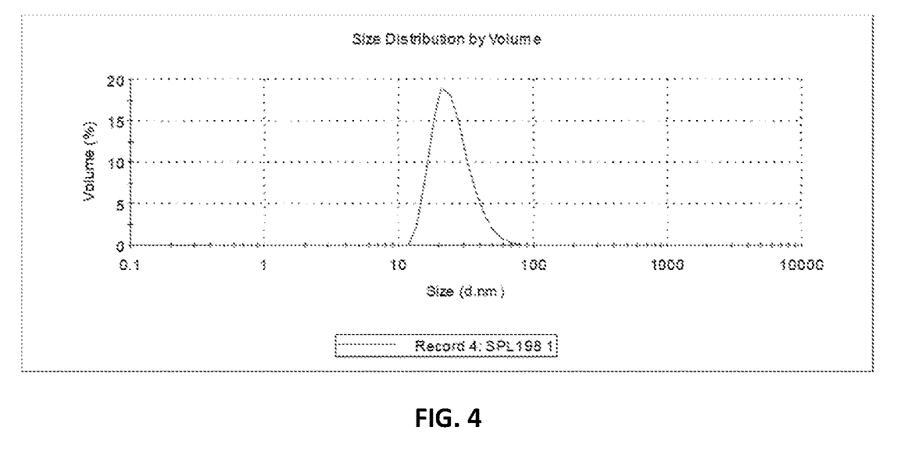
Figure 5:
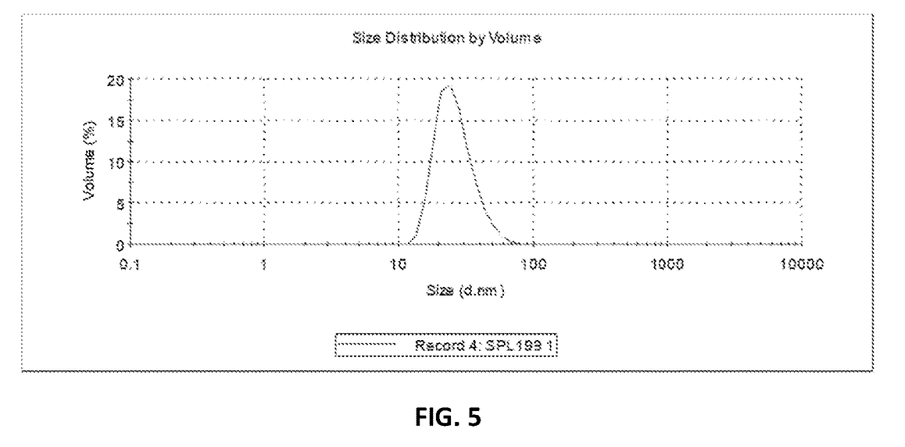
Figure 6:
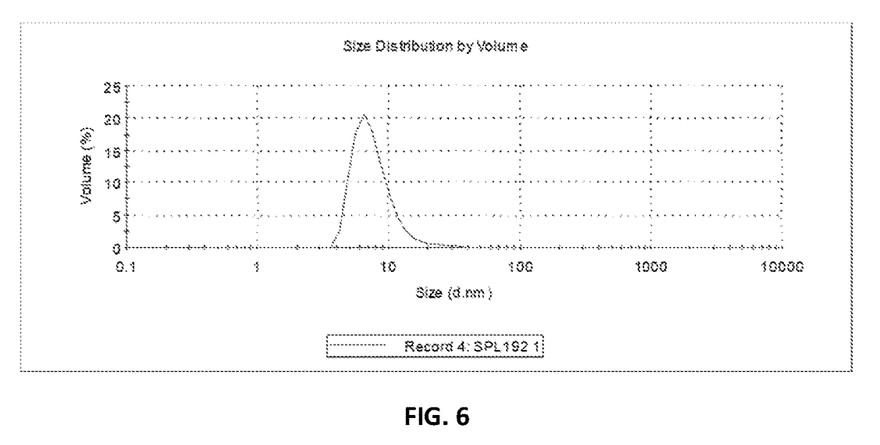
Figure 7:
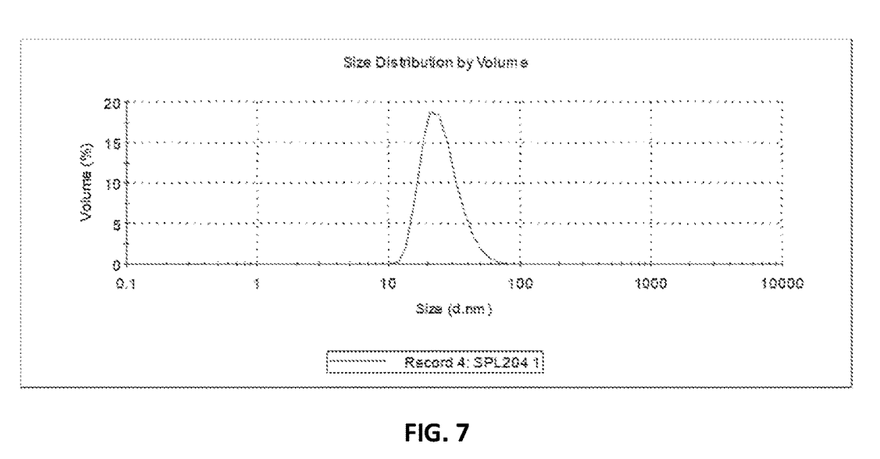
Figure 8:
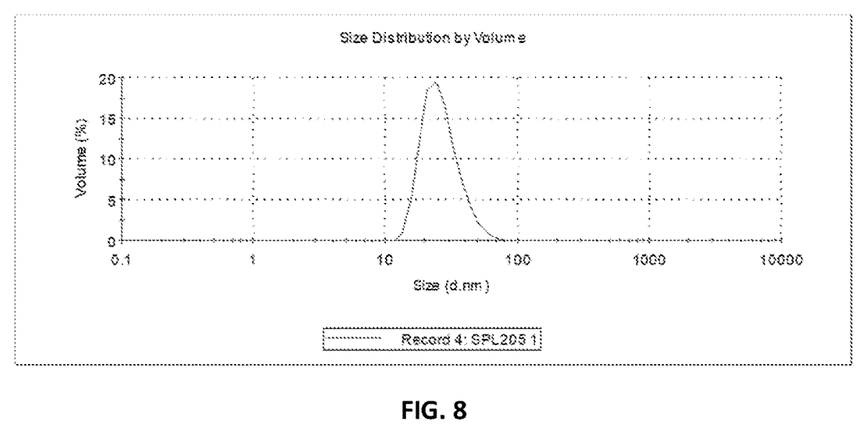

The current invented multi-layer nanoparticles, nanoemulsions, and creams made through invented novel manufacturing processes (methods) are suitable vehicles, and can deliver the encapsulated compounds through multiple skin 
layers to tissues and cells, and have profound clinical effects. The mechanism by which the multi-layer nanoparticles and nanoemulsions crossing skin layers by itself is believed to involve the above mentioned three trans-dermal delivery pathways: hair follicular channels, inter-cellular space and intra-cellular space or membranes. Along the skin penetration paths through lipophilic and hydrophilic membranes, multi-layer small nanoparticles and nanoemulsions are travelled (and massaged with hand, fingers) into the inner layers of skin; the encapsulated compounds inside the nanoparticles (on the surface of nanoparticles and nanoemulsions, and between the multi-layers of nanoemulsions) are gradually released into the different layers of the penetration pathways. Interactions between the skin's multiple lipophilic & hydrophilic layers and the multi-layer nanoparticles & nanoemulsions help absorption of active ingredients and the nanoparticles to travel across multiple skin barriers. Because massaging the skin in application is a gentle and natural process, natural skin structure is intact (compared to micro-needle and injectable), large bio-molecules activity is retained until released at the inner skin layers and inside cells where clinical effects are most profoundly produced. This mechanism can also explain the evident effects of anti-wrinkle, skin firming, skin whitening and wounds healing observed in individuals using these formulations.

This invention relates to nano-particles and nano-emulsions, methods of making and using the same. In particular, this relates to special multi-layer water in oil then in water nano-particle encapsulated with active ingredients and wrapped with a cream. In general the nanoparticles can be prepared by using method such as electrochemical [12], ultrasounic and microfluidics [13, 14, 15], etc. This invention reports here a novel method to prepare smaller nanoparticles (such as less than 10 nm, 20 nm, 30 nm, 40 nm or so) with active ingredients encapsulated within. These nanoparticles are surrounded by slightly larger nanoparticles (such as less than 30 nm, 40 nm, 50 nm, 60 nm or so) with active ingredients encapsulated. Finally these nanoparticles are surrounded by a cream to form stable nanoemulsions with particle size from 10 to 150 nm, but mainly from 20 to 50 nm. The active ingredients can be encapsulated inside nanoparticles, between the layers of nanoparticles, inside the nanoemulsions and on the surface of nanoparticles and nanoemulsions.

The following strategy has been applied to make the multi-layer nanoemulsions that contain small nanoparticles which further contain even smaller nanoparticles within themselves. Mild processes and gentle conditions have been used in developing the entire manufacturing process. First, adding the aqueous solution of active ingredients including bio-molecules into a stirring oil phase generates water-in-oil (W/O) nanoparticles (smaller nanoparticles) with size less than 10 nm, 20 nm, sometimes less than 30 nm, or 50 nm; Second, adding these smaller nanoparticles into a stirring aqueous phase containing active ingredients such as bio-molecules generates oil-in-water (O/W) nanoparticles (small nanoparticles) with size less than 30 nm, 40 nm, sometimes less than 50 nm, 60 nm, 80 nm; Thirdly, a cream (such as the Cream 1 as listed in this specification or other creams as listed in the experiment section of this specification) is added into the formed small nano-particles to form multi-layer nano-particles and nano-emulsions that has a size of less than 30 nm, 40 nm, 50 nm, 60 nm, sometimes less than 80 nm, but usually less than 100 nm or sometimes less than 150 nm. The multi-layer nanoparticles and nanoemulsions normally look transparent or semi-transparent, sometimes less transparent. Within this art of preparation of nanoparticles and nanoemulsions, no sophiscated equipment was used. Magnetic stirring, mechanical stirring or equivalent device can be employed. The end product of multi-layer nanoparticles and nanoemulsions can be obtained fairly easily from this method and can be used for broad applications in pharmaceutical, medical and cosmetics fields depending on the properties of the active ingredients used. The above prepared multi-layer nanoparticles and nanoemulsions are shown in FIG. 1, skin structure is shown in FIG. 2A, and how the invented multi-layer nanoparticles and nanoemulsions to cross the skin is shown in FIG. 2B.

BRIEF DESCRIPTION OF THE DRAWINGS

FIG. 1 presents a simplified scheme of multi-layer nanoparticles and nanoemulsions. 1 represents oil phase, 2 represents water phase, 3 represents encapsulated ingredients (shown as small dots in all layers), 4 represents oil phase, 5 represents water phase, 6 represents oil phase.

FIG. 2A presents a simplified scheme of skin structure/layers. 7 represents oil phase, 8 represents water phase, 9 represents oil phase, 10 represents water phase, 11 represents oil phase, 12 represents water phase, 13 represents oil phase, 14 represents water phase, 15 represents oil phase, 16 represents water phase, 17 represents oil phase, 18 represents Stratum corneum layer, 19 represents Epidermi layer, 20 represents Dermis layer, 21 represents cells, and 22 represents hair follicles/pores.

FIG. 2B presents a simplified scheme of multi-layer nanoparticles and nanoemulsions crossing skin layers to cells. 23 represents multi-layer nanoparticles and nanoemulsions before entering the skin, 24 represents Stratum Corneum, 25 represents Epidermi, 26 represents Dermis, 27 represents cells under the skin, 28 represents enlarged nanoparticles and nanoemulsions before entering the skin, 29 represents released ingredients after crossing Stratum Corneum, 30 represents multi-layer nanoparticles and nanoemulsions that crossed Stratum Corneum, 31 represents released ingredients after crossing Epidermi, 32 represents multi-layer nanoparticles and nanoemulsions that crossed Epidermi, 33 represents multi-layer nanoparticles and nanoemulsions that crossed Dermis, 34 represents released ingredients after crossing Dermis, 35 & 35' represent single cells, 36 represents released ingredients inside cell, 37 represents multi-layer nanoparticles and nanoemulsions inside cell, 38 & 38' represents nucleus, and 39 represents released ingredients inside nucleus.

FIG. 3 illustrates representative Sample Size Graph 1 (W/O, SPL198a): Z (average)=12.52 nm; D (v, 0.1)=4.63 nm, D (v, 0.5)=6.82 nm, D (v, 0.9)=10.40 nm, Note: Z (average) is the averaged particle size by intensity; D (v, 0.1), D (v, 0.5) and D (v, 0.9) are the particle size values at 10%, 50% and 90% of total particles volume, respectively.

FIG. 4 illustrates representative Sample Size Graph 2 (O/W, SPL198): Z (average)=31.91 nm; D (v, 0.1)=16.50 nm, D (v, 0.5)=23.70 nm, D (v, 0.9)=37.60 nm.

FIG. 5 illustrates representative Sample Size Graph 3 (NPs w/TR2, SPL199): Z (average)=32.48 nm; D (v, 0.1) =17.40 nm, D (v, 0.5)=24.90 nm, D (v, 0.9)=39.10 nm.

FIG. 6 illustrates representative Sample Size Graph 4 (W/O, SPL192): Z (average)=13.54 nm; D (v, 0.1)=5.00 nm, D (v, 0.5)=7.01 nm, D (v, 0.9)=11.20 nm.

FIG. 7 illustrates representative Sample Size Graph 5 (O/W, SPL204): Z (average)=31.19 nm; D (v, 0.1)=16.60 nm, D (v, 0.5)=23.90 nm, D (v, 0.9)=37.50 nm.

FIG. 8 illustrates representative Sample Size Graph 6 (NPs w/TR2, SPL205): Z (average)=32.62 nm; D (v, 0.1) =17.50 nm, D (v, 0.5)=25.00 nm, D (v, 0.9)=39.10 nm.

Figure 9:
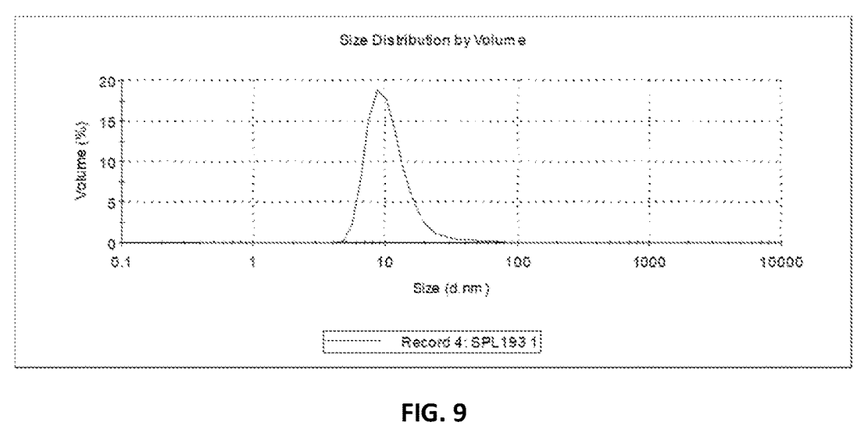

FIG. 9 illustrates representative Sample Size Graph 7 (W/O, SPL193): Z (average)=25.45 nm; D (v, 0.1)=6.82 nm, D (v, 0.5)=9.86 nm, D (v, 0.9)=16.80 nm.

Figure 10:
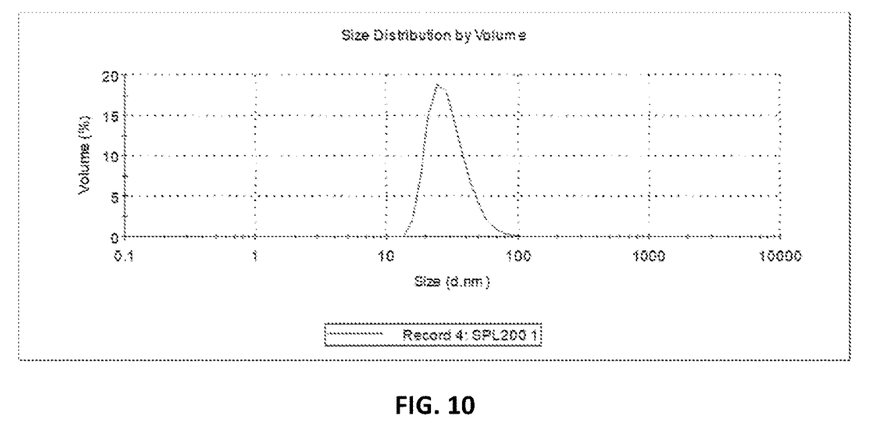

FIG. 10 illustrates representative Sample Size Graph 8 (O/W, SPL200): Z (average)=37.13 nm; D (v, 0.1)=19.20 nm, D (v, 0.5)=27.70 nm, D (v, 0.9)=44.00 nm.

Figure 11:
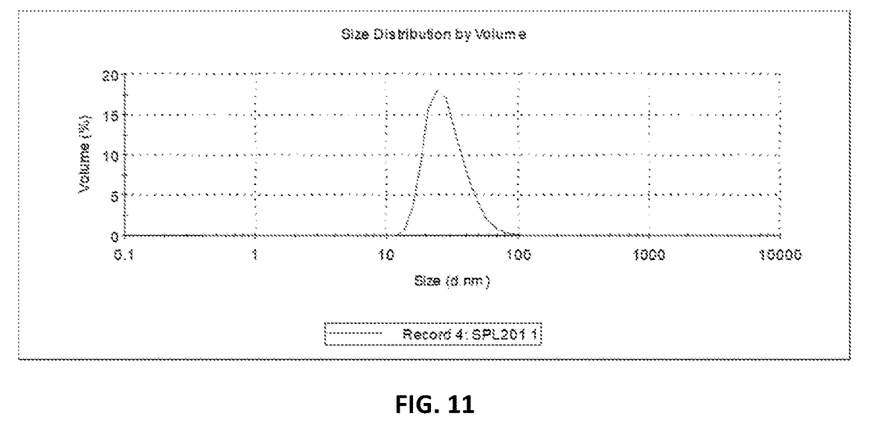

FIG. 11 illustrates representative Sample Size Graph 9 (NPs w/TR2, SPL201): Z (average)=37.31 nm; D (v, 0.1) =18.50 nm, D (v, 0.5)=27.10 nm, D (v, 0.9)=43.80 nm.

Figure 12:
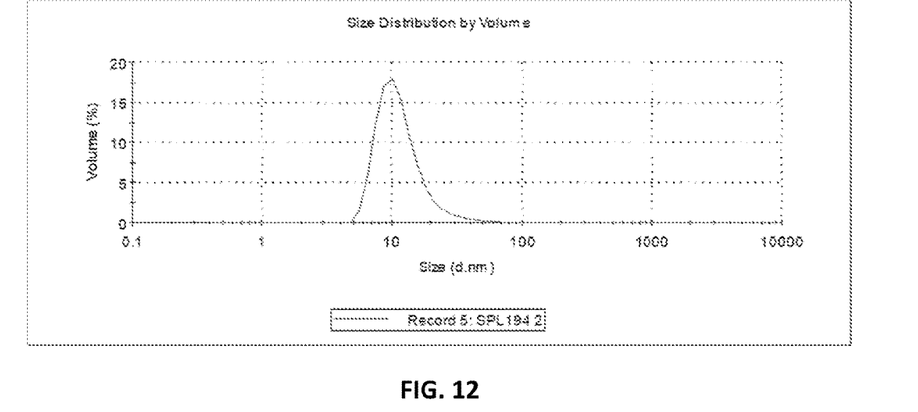

FIG. 12 illustrates representative Sample Size Graph 10 (W/O, SPL194): Z (average)=20.92 nm; D (v, 0.1)=7.11 nm, D (v, 0.5)=10.50 nm, D (v, 0.9)=18.00 nm.

Figure 13:
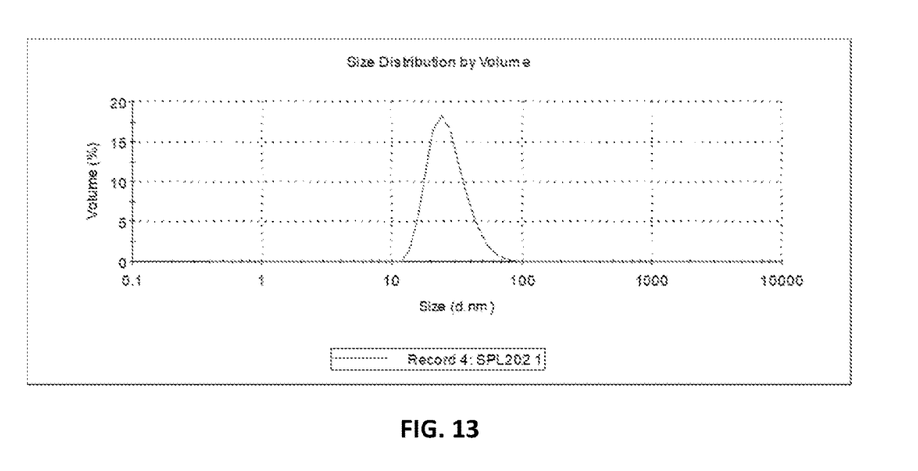

FIG. 13 illustrates representative Representative Sample Size Graph 11 (O/W, SPL202): Z (average)=37.14 nm; D (v, 0.1)=17.50 nm, D (v, 0.5)=25.80 nm, D (v, 0.9)=41.50 nm.

Figure 14:
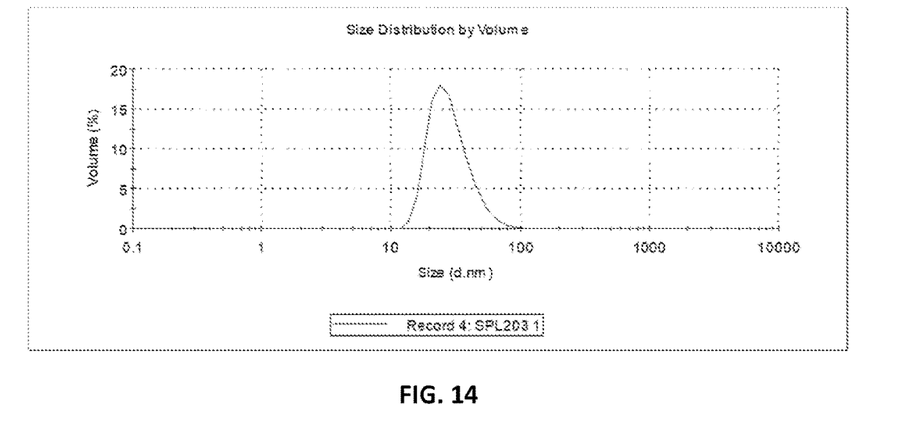

FIG. 14 illustrates representative Sample Size Graph 12 (NPs w/TR2, SPL203): Z (average)=37.28 nm; D (v, 0.1) =18.30 nm, D (v, 0.5)=26.70 nm, D (v, 0.9)=43.40 nm.

Figure 15:
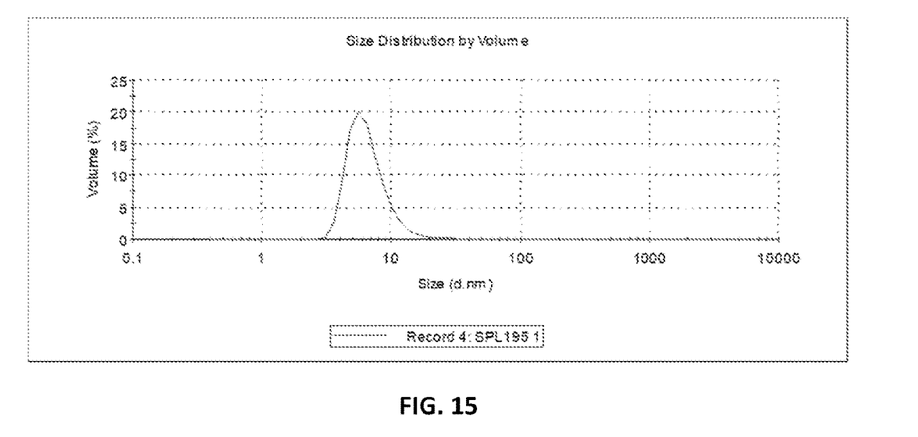

FIG. 15 illustrates representative Sample Size Graph 13 (W/O, SPL195): Z (average)=10.45 nm; D (v, 0.1)=4.31 nm, D (v, 0.5)=6.10 nm, D (v, 0.9)=9.76 nm.

Figure 16:
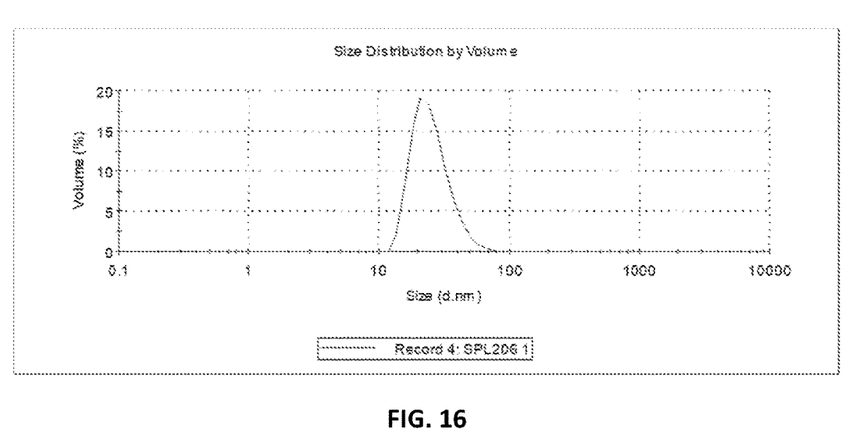

FIG. 16 illustrates representative Sample Size Graph 14 (O/W, SPL206): Z (average)=31.65 nm; D (v, 0.1)=16.50 nm, D (v, 0.5)=23.70 nm, D (v, 0.9)=37.50 nm.

Figure 17:
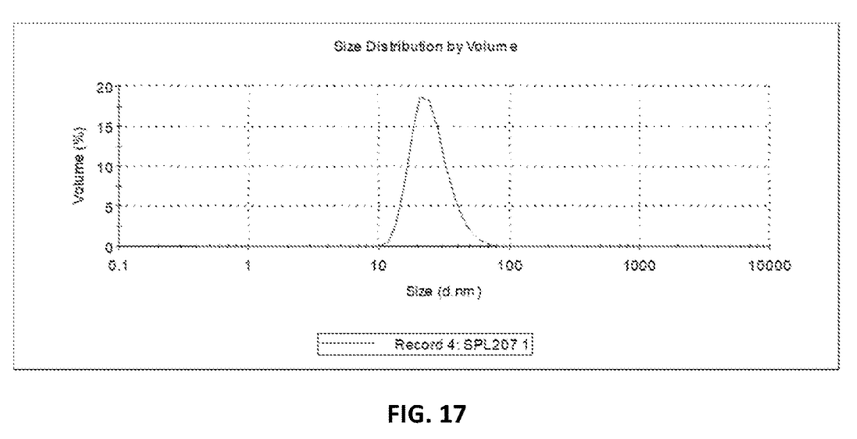

FIG. 17 illustrates representative Sample Size Graph 15 (NPs w/TR2, SPL207): Z (average)=32.27 nm; D (v, 0.1) =16.30 nm, D (v, 0.5)=23.80 nm, D (v, 0.9)=37.50 nm.

Figure 18:
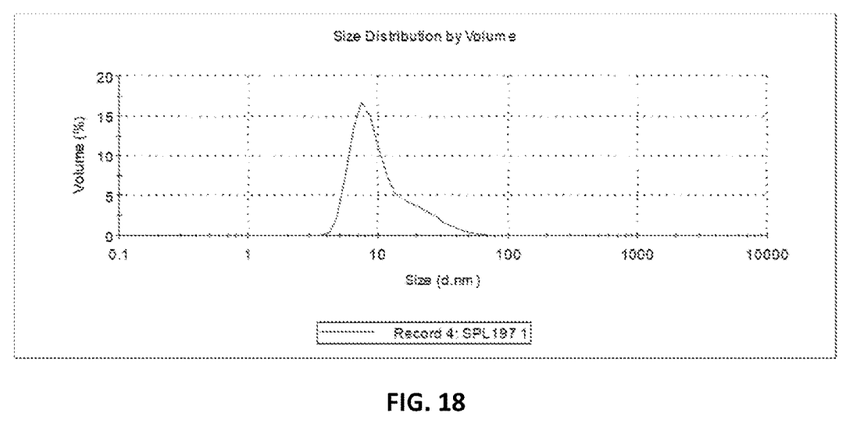

FIG. 18 illustrates representative Sample Size Graph 16 (W/O, SPL197): Z (average)=19.90 nm; D (v, 0.10)=5.92 nm, D (v, 0.50)=8.94 nm, D (v, 0.90)=22.30 nm.

Figure 19:
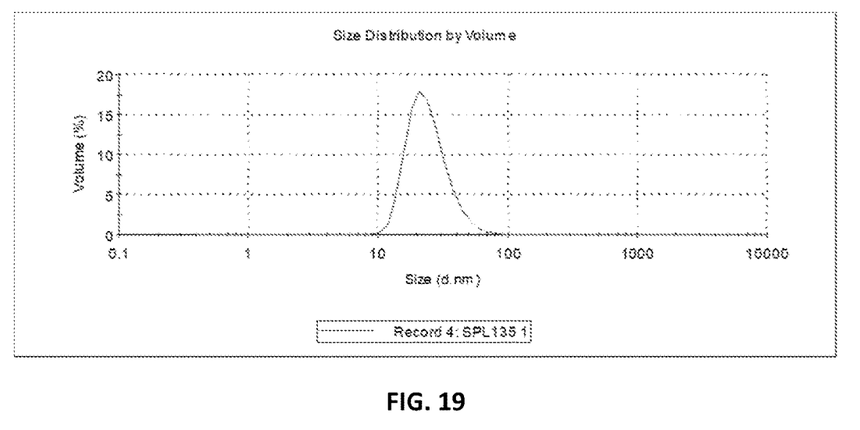

FIG. 19 illustrates representative Sample Size Graph 17 (O/W, SPL135): Z (average)=33.82 nm; D (v, 0.10)=15.50 nm, D (v, 0.50)=22.90 nm, D (v, 0.90)=37.10 nm.

Figure 20:
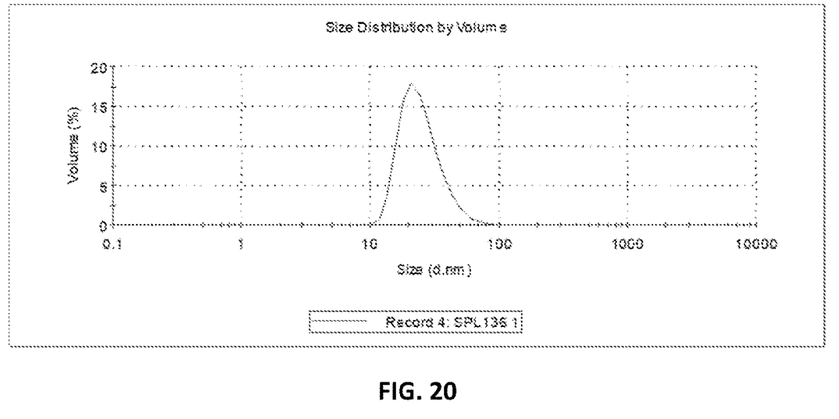

FIG. 20 illustrates representative Sample Size Graph 18 (NPs w/TR2, SPL136): Z (average)=35.10 nm; D (v, 0.10) =15.80 nm, D (v, 0.50)=23.20 nm, D (v, 0.90)=38.20 nm.

BEST MODE FOR CARRYING OUT THE INVENTION

Many experiments were carried out and following examples are given herein to illustrate the process and some results. The particle sizes were measured on Malvern Light Scattering Particle Sizer ZS90 instrument.

Experiment 1: One Surfactant System A (Octanoic Acid Decanoic Acid Ester of Glycerol, Oil A)

Octanoic acid decanoic acid ester of glycerol (2 g) was added in Cremophor EL (3 g) and mixed well at room temperature. Then an aqueous solution of active ingredients (0.25 g) such as hyaluronic acid (0.5%) was added in and mixed well. The resulting clear solution is measured for particle size and zeta potential on a Malvern Particle Sizer Instrument. The particle size is 12.52 nm by intensity (z average) and 4.63 nm to 10.40 nm by volume distribution (Graph 1). In a separate container this clear solution was added into a 45 g aqueous hyaluronic acid solution (0.5%) with stirring and mixed well. The resulting material is transparent to bluish solution which has a particle size of 31.91 nm by intensity (z average) and 16.50 nm to 37.60 nm by volume distribution (Graph 2). To this nanoparticle solution, a cream containing emulsifier Pemulen TR2 (2 g) was added to further stabilize the nanoparticles and mixed well. It gave the formed final nanoemulsions. It is almost transparent, bluish liquid with particle size of 32.48 nm by intensity (z average) and from 17.40 nm to 39.10 nm by volume distribution (Graph 3).

Experiment 2: One Surfactant System B (Labrafac Lipophile WL 1349, Oil B)

Cremophor EL (3 g) was added in Labrafac Lipophile WL 1349 oil (2 g) in a beaker under stirring at room temperature and mixed well. Then an aqueous solution (0.25 g) contains active ingredients such as hyaluronic acid (0.5%) was added into the mixture and mixed well. The particle size of the resulting clear solution was measured by Malvern Particle Sizer Instrument. The size of zeta potential is 13.54 nm by intensity (z average) and 5.00 nm to 11.20 nm by volume distribution (Graph 4). In another container, this clear solution was added into 45 g solution of hyaluronic acid (0.5%) with stirring in and mixed well. The resulting material is transparent to bluish solution which has a particle size of 31.19 nm by intensity (z average) and 16.60 nm to 37.50 nm by volume distribution (Graph 5). The formed nanoparticles were further stabilized by emulsifier Permulen TR2 containing cream (2 g) mixed well to give final nanoemulsions. This nanoemulsion is almost transparent bluish liquid with particle size of 32 nm by intensity (z average) and 18 nm to 38 nm by volume distribution (Graph 6).

Experiment 3: Two Surfactant System (Cremophor EL and Tween-20)

Octanoic acid decanoic acid ester of glycerol (2 g) in a beaker, Cremophor EL (2.0 g) and polysorbate-20 (Tween-20, 1 g) was added in and mixed well at room temperature. An aqueous solution of active ingredients such as hyaluronic acid (0.25 g) was added in and mixed well. The particle size of resulting clear solution was measured on a Malvern Particle Size Instrument. It is 25.45 nm by intensity (z average) and 6.82 nm to 16.80 nm by volume distribution (Graph 7). This clear solution was added into 45 g aqueous hyaluronic acid (0.5%) solution with stirring and mixed well. The resulting nanoemulsion is transparent and bluish in color. It has a particle size of 37.13 nm by intensity (z average) and 19.20 nm to 44.00 nm by volume distribution (Graph 8). The formed nanoparticles were further stabilized by emulsifier Permulen TR2 containing cream (2 g) mixed well to give final nanoemulsions. This nanoemulsion is translucent bluish liquid with particle size of 37.31 nm by intensity (z average) and 18.50 nm to 43.80 nm by volume distribution (Graph 9).

Experiment 4: More than Two Surfactant System

Octanoic acid decanoic acid ester of glycerol (2. g) in a container with stirring, Cremophor EL (1 g) and polysorbate-80 (Tween-80, 1 g) and polysorbate-20 (Tween-20, 1 g) were added in and mixed well at room temperature. Then an aqueous solution (0.25 g) of active ingredients such as hyaluronic acid (0.5%) was added in and mixed well. Particle size of the resulting clear solution was measured on a Malvern Particle Sizer Instrument. It is 20.92 nm by intensity (z average) and 7.11 nm to 18.00 nm by volume distribution (Graph 10). This clear solution was added into 45 g aqueous solution containing active ingredients of hyaluronic acid (0.5%), stirred and mixed well. The resulting material is transparent to bluish solution which has a particle size of 37.14 nm by intensity (z average) and 17.50 nm to 41.50 nm by volume distribution (Graph 11). The formed nanoparticles were further stabilized by emulsifier Permulen TR2 containing cream (2 g) mixed well to give final nanoemulsion. This nanoemulsion is translusent bluish liquid with particle size of 37.28 nm by intensity (z average) and 18.30 nm to 43.40 nm by volume distribution (Graph 12).

Experiment 5: Nanoemulsion System with Hydrophilic Stabilizers

Octanoic acid decanoic acid ester of glycerol (2 g) in a container with stirring, Cremophor EL (3 g) was added in and mixed well at room temperature. Then an aqueous solution (0.25 g) of active ingredients such as hyaluronic acid (0.5%) and glycerol (1%) was added in and mixed well. Particle size of the resulting clear solution was measured on a Malvern Particle Size Instrument. It is 10.45 nm by intensity (z average) and 4.31 nm to 9.76 nm by volume distribution (Graph 13). This clear solution was added into an aqueous solution (45 g) containing active ingredients such as hyaluronic acid (0.5%) and glycerol (1%) stirred and mixed well. The resulting material is transparent to bluish solution which has a particle size of 31.65 nm by intensity (z average) and 16.50 nm to 37.50 nm by volume distribution (Graph 14). The formed nanoparticles were further stabilized by emulsifier Permulen TR2 containing cream (2 g) mixed well to give final nanoemulsion. This nanoemulsion is translucent bluish liquid with particle size of 32.27 nm by intensity (z average) and 16.30 nm to 37.50 nm by volume distribution (Graph 15).

Experiment 6: Different Oils Phase with One Surfactant System A

Soybean oil (1 g, or tea oil) and octanoic acid decanoic acid ester of glycerol (1 g) in a container, Cremophor EL (3 g) was added in under stirring and mixed well at room temperature. An aqueous solution (0.25 g) of active ingredients such as hyaluronic acid (0.5%) was added in and mixed well. The resulting clear solution is measured for particle size and zeta potential on a Malvern Particle Size Instrument, the size is 19.90 nm by intensity (z average) and 5.92 nm to 22.30 nm by volume distribution (Graph 16). This clear solution was' added into aqueous solution (45 g) of active ingredients such as hyaluronic acid (0.5%) stirred and mixed well. The resulting material is transparent bluish solution which has a particle size of 33.82 nm by intensity (z average) and 15.50 nm to 37.10 nm by volume distribution (Graph 17). The formed nanoparticles were further stabilized by emulsifier Permulen TR2 containing cream (2 g) mixed well to give final nanoemulsion. The formed nanoemulsion is translucent bluish liquid with particle size of 35.10 nm by intensity (z average) and 15.80 nm to 38.20 nm by volume distribution (Graph 18).

Preparation of Cream 1

Total 200 gram cream was prepared from this batch. Phase 1: In a beaker purified water (135 g), methyparaben (0.4 g), glycerin (3 g) and phenoxyethenol (6.0 g) was mixed well at 70° C. Phase 2: In a separate container, mineral oil (5 g), avocado oil (5 g), isopropyl myristate (5 g), white petrolatum (4 g), vitamin E (4.6 g), emulsifying wax (18 g), bees wax (7 g), cetearyl alcohol (3 g), ethylhexylglycerin (2 g) and propylparaben were heated to 70° C., melted and mixed well. Transfer Phase 2 at 70° C. into Phase 1 and mix well at 70° C., stir and cool to room temperature. From above processes, nanoparticles and nanoemulsions with particles size less than 150 nm, less than 100 nm, less than 80 nm, less than 50 nm, less than 30 nm, less than 20 and 10 nm were successfully prepared. These nanoparticles and nanoemulsions materials are stable under room temperature, under elevated temperature and under lower temperatures such as frozen (<0° C., see Tables 1-3).

Stability Test of Cream 1:

A. Freeze-Thaw Cycle Stability Test: Nanoemulsions prepared from above process were placed at room temperature for 24 hours, particle size was measured (29.57 nm), then placed at −20° C. for 24 hours. The particle size was measured (31.38 nm). The process was repeated for 3 times, the particle size was 31.38 nm.

TABLE 1

Freeze-Thaw Cycle Stability (SPL92)

| Freeze/Thaw Cycle | Temp. (° C.) | Particle Size (nm) |
|---|---|---|
| Time Zero (initial) | RT (25° C.) | 29.57 |
| $1^{st}$ Cycle | −20 | 32.78 |
| $2^{nd}$ Cycle | −20 | 31.24 |
| $3^{rd}$ Cycle | −20 | 31.38 |

Note:
Each cycle consists 24 hours storage at RT (25° C.) followed by 24 hours storage at −20° C.

B: Storage Stability at Room Temperature (RT) and Refrigerated Condition

The nanoemulsions were prepared from above process and storage stability was measured by its size distribution under the room temperature (25° C.) and under the refrigerated condition (2-8° C.). The result is listed below in Table 2, and as shown the multi-layer nanoemulsions and nanoparticles are fairly stable for many months in storage.

TABLE 2

Storage Stability under Different Temperature (SPL107)

| Storage Time (Day) | Particle size (nm) At 25° C. | Particle size (nm) At 2-8° C. |
|---|---|---|
| 0 | 66.77 | 66.77 |
| 9 | 58.22 | 61.54 |
| 16 | 49.18 | 50.41 |
| 32 | 54.01 | 47.43 |
| 130 | 42.97 | 48.91 |

C: Stability under Elevated Temperature

The nanoemulsions were prepared from above mentioned processes. The stabilities were tested under accelerated conditions. Under elevated temperature, the nanoemulsions and nanoparticles are very stable for 22 days and beyond (see Table 3 below).

TABLE 3

Stability under 40° C. (SPL104)

| Storage Time (Day) | Particle size (nm) |
|---|---|
| Time Zero (Initial) | 80.76 |
| 4 | 77.89 |
| 22 | 82.84 |

Conclusion: The multi-layer nanoparticles and nanoemulsions prepared by present method as described above are very stable under various temperature conditions for storage and usage. The particle size remained constant which is the indicator for its long-term stability. The physical observations including visual inspection on color, transparency, liquid uniformity and viscosity also confirmed the physical-chemical stability of these nano-materials.

INDUSTRIAL APPLICABILITY

Compositions and Usage:

The contents encapsulated in the multi-layer nanoparticles and nanoemulsions by our method include broad range of biological molecules and organic compounds with either lipophilic or hydrophilic characteristics. The lipophilic (or hydrophobic) ingredients such as palmitoyl-pentapeptide KTTKS and other palmitoyl oligo-peptides are dissolved in the oil and surfactant phase, the hydrophilic (or water soluble) ingredients such as hyaluronic acid and water soluble peptides are dissolved in the aqueous phase. From above preparation process, both water insoluble ingredients and water soluble ingredients are prepared in nanoparticles and nanoemulsions with particle size less than 150 nm, 100 nm, 80 nm, 50 nm, 30 nm, 20 nm and 10 nm. They are stable at various storage conditions such as at lower temperatures (<0° C.), room temperature, and elevated temperatures (>40° C.). Thus more ingredients can be encapsulated inside the nanoparticles and nanoemulsions for different usages and applications.

The active ingredients contained in the multi-layer nanoparticles and nanoemulsions is selected from Palmitoyl pentapeptide KTTKS, Palmitoyl tetrapeptide GQPR, Palmitoyl GHK, other pamitoyl-oligopeptides, Hexapeptide argireline, Snap-8 octapeptide, other oligpeptides, hyaluronic acid, allantoin, niacinamide, aloe vera, Cu-GHK tripeptide, and di-peptides. Also, the nanoparticles and nanoemulsions contain active ingredients selected from aloe vera, allantoin, niacinamide, Q10, resveratrol, vitamin C, vitamin D, vitamin E, hexapeptide argireline, octa-peptide Snap-8, oligo-peptides, Cu-GHK, palmitoyl-GHK, palmitoyl-KTTKS, palmitoyl-GQPR, palmitoyl-oligopeptides, stem cells, stem cell matrix, stem cell growth factors, plant stem cell growth factors, human stem cell growth factors, insulin, cell growth factors, epidermal cell growth factors (EGFs), fibroblast cell growth factors (FGFs), keratinocyte growth factors (KGFs), 5-floro-uracil, diacarbazine, celecoxib, rofecoxib, silver ions (Ag+) such as AgNO3, ibuprofen, minocycline, tetracycline, doxycycline, oxytetracycline, estriol, estradiol, progesterone.

One of the usages was to apply the prepared encapsulated multi-layer nanoparticles and nanoemulsions by above mentioned methods with following three compositions 1, 2 and 3 on human skin. Depending on the active ingredients added into the oil surfactant phase and the aqueous phase, skin wrinkle-reducing and firming-up effect (Composition 1), skin whitening, and skin firming-up effect (Composition 2), and speedy (within 13 days) skin bleeding wounds healing effect without scars left (Composition 3) were observed within a few weeks' time frame following twice per day application on human subject skin wounds areas. Some of the results are shown below:

Composition 1
Oil+Surfactant Phase: Palmitoyl pentapeptide KTTKS, Palmitoyl tetrapeptide GQPR, Palmitoyl GHK, and other pamitoyl-oligopeptides.
Aqueous Phase: Hexapeptide argireline, Snap-8 octapeptide and other oligpeptides, hyaluronic acid, allantoin and niacinamide, aloe vera.
Usage: Topical facial skin application of these nanoparticles and nanoemulsions from Composition 1, twice per day, about 1 ml each time.
After 8 weeks topical application of Multi-layer Nanoemulsions from Composition 1, wrinkle reduction and skin firming-up are observed comparing before usage.
Composition 2
Oil+Surfactant Phase: Palmitoyl GHK and other oligopeptides
Aqueous Phase: Cu-GHK tripeptide, di-peptides and other oligopeptides, hyaluronic acid, allantoin and niacinamide, aloe vera.
Usage: Topical facial skin application of these nanoparticles and nanoemulsions from Composition 2, twice per day, about 1 ml each time.
After 3 weeks topical application of Multi-layer Nanoemulsions from Composition 2, wrinkle reduction and saggy skin firming-up improvement are observed comparing before usage.
Composition 3
Oil+Surfactant Phase: Palmitoyl GHK
Aqueous Phase: Cu-GHK tripeptide and di-peptides, hyaluronic acid, allantoin and niacinamide, aloe vera.
Usage: Topical skin application of these nanoparticles and nanoemulsions from Composition 3, twice per day, about 1 ml each time to the wounds areas. Apply more if needed due to the bigger skin wounds areas.
After 13 days topical application of Multi-layer Nanoemulsions from Composition 3 to face and hand with bleeding and scars, skin bleeding & wounds healing with no scars left are observed comparing before usage.
Clinical Effects:
Due to quick and effective skin penetration of active ingredients via topical application of the prepared nanoparticles and nanoemulsions by the above prescribed methods, the multi-layer nanoparticles and nanoemulsions from the above three compositions (but are not limited to these three compositions as shown above) have profound clinical skin condition improvement effects. Typical clinical results from these studies are shown with quick and significant effects.

CONCLUSIONS

New multi-layer nanoparticles and nanoemulsions were prepared with the novel preparation methods described in above body text. These multi-layer nanoparticles & nanoemulsions encapsulated with cosmeceutical and pharmaceutical active ingredients can travel deep into the skin layers, tissues and cells, and have profound clinical effects observed on human subjects. The nano-materials, preparation methods, the compositions and the creams are unique technique & process, and can be applied broadly in pharmaceutical, cosmetics, dietary supplement, nutraceutical, and sports medicine fields.

Although the multi-layer nanoparticles and nanoemulsions and the method of using the same according to the present invention has been described in the foregoing specification with considerable details, it is to be understood that modifications may be made to the invention which do not exceed the scope of the appended claims and modified forms of the present invention done by others skilled in the art to which the invention pertains will be considered infringements of this invention when those modified forms fall within the claimed scope of this invention.

What is claimed is:
1. A nanoemulsion, comprising: a nanoparticle having one layer of particle enclosing another layer of particle, wherein an innermost layer of particle includes a water-in-oil nanoparticle enclosed by an oil-in-water nanoparticle, wherein the nanoparticle further comprises one or more materials selected from a group consisting of an active ingredient for a topical application, a cosmetic and cosmeceutical ingredient, and a pharmaceutical and nutraceutical ingredient, encapsulated within or situating on a surface of each layer in the nanoparticle; and an outermost layer wrapped around the nanoparticle, wherein the outermost layer contains a cream formed by the steps of first preparing a phase 1 by mixing purified water, methyparaben, glycerin and phenoxyethanol in a beaker at a temperature; preparing a phase 2 by heating and mixing mineral oil, avocado oil, isopropyl myristate, white petrolatum, vitamin E, emulsifying wax, bees wax, cetearyl alcohol, ethylhexylglycerin and propylparaben to the temperature in a separate container; transferring the mixture from phase 2 at the temperature into phase 1, mixing at the temperature with stirring, and cooling to room temperature, thereby forming the cream.

2. The nanoemulsion according to claim 1, wherein:
the water-in-oil nanoparticle has a particle size less than 30 nm,
the oil-in-water nanoparticle has a particle size less than 80 nm, and
the nanoemulsion has a particle size less than 150 nm.

3. The nanoemulsion according to claim 2, wherein:
the water-in-oil nanoparticle has a particle size less than 5 nm,
the oil-in-water nanoparticle has a particle size less than 30 nm, and
the nanoemulsion has a particle size less than 50 nm.

4. The nanoemulsion according to claim 1, wherein:
the active ingredient is selected from Palmitoyl pentapeptide KTTKS, Palmitoyl tetrapeptide GQPR, Palmitoyl GHK, other pamitoyl-oligopeptides, Hexapeptide argireline, acetyl octapeptide-3, other oligpeptides, hyaluronic acid, allantoin, niacinamide, aloe vera, Cu-GHK tripeptide, and di-peptides.

5. The nanoemulsion according to claim 4, wherein:
the active ingredient includes hyaluronic acid encapsulated in aqueous phase with a concentration range from 0.01% to 10% by weight.

6. The nanoemulsion according to claim 1, wherein:
the active ingredient is selected from aloe vera, allantoin, niacinamide, Q10, resveratrol, vitamin C, vitamin D, vitamin E, hexapeptide argireline, acetyl octapeptide-3, oligo-peptides, Cu-GHK, palmitoyl-GHK, palmitoyl-KTTKS, palmitoyl-GQPR, palmitoyl-oligopeptides, stem cells, stem cell matrix, stem cell growth factors, plant stem cell growth factors, human stem cell growth factors, insulin, cell growth factors, epidermal cell growth factors (EGFs), fibroblast cell growth factors (FGFs), keratinocyte growth factors (KGFs), 5-floro-uracil, diacarbazine, celecoxib, rofecoxib, silver ions (Ag+) such as AgNO3, ibuprofen, minocycline, tetracycline, doxycycline, oxytetracycline, estriol, estradiol, and progesterone.

7. The nanoemulsion according to claim 1, wherein the active ingredient for the topical application includes:
pamitoyl-oligopeptides including Palmitoyl pentapeptide KTTKS, Palmitoyl tetrapeptide GQPR, and Palmitoyl GHK, in an oil phase; and
Hexapeptide argireline, Snap-8 octapeptide, hyaluronic acid, allantoin, niacinamide, and aloe vera, in an aqueous phase, for the topical application with anti-wrinkle, wrinkle-reducing, anti-ageing, and skin firming effect.

8. The nanoemulsion according to claim 1, wherein the active ingredient for the topical application includes:
Palmitoyl GHK in an oil phase; and
Cu-GHK tripeptide, di-peptides, hyaluronic acid, allantoin, niacinamide, and aloe vera in an aqueous phase, for the topical application with anti-wrinkle, wrinkle-reducing, anti-ageing, and skin firming effect.

9. The nanoemulsion according to claim 1, wherein the active ingredient for the topical application includes:
Palmitoyl GHK in an oil phase, and
Cu-GHK tripeptide, di-peptides, hyaluronic acid, allantoin, niacinamide, and aloe vera in an aqueous phase, for the topical application with anti-inflammatory and speedy skin wounds healing effect.

10. The nanoemulsion according to claim 1, being formed by: adding an aqueous phase into a stirring oil and surfactant phase to form the water-in-oil nanoparticle; adding the water-in-oil nanoparticle into a stirring aqueous phase to form the oil-in-water nanoparticle; preparing the cream; and mixing the cream with the oil-in-water nanoparticle by stirring to form the nanoemulsion, wherein one of a magnetic stirring and a mechanical stirring is employed with a stirring rate ranging from 10 rpm to 5,000 rpm at a temperature ranging from 5 C to 95° C.

11. The nanoemulsion according to claim 10, wherein:
the stirring oil and surfactant phase includes an oil, selected from octanoic acid decanoic acid ester of glycerol, capric and caprylic acid triglycerides, soybean oil, tea oil, sunflower seed oil, vegetable oil, fish oil, sesame oil, animal lipid oil, Vitamin E; wherein said surfactant is selected from macrogol-35-glycerolrizinoleat, polysorbate-20 (Tween-20), polysorbate-60 (Tween-60), polysorbate-80 (Tween-80), sorbitane monopalmitate, and PEG.

12. The nanoemulsion according to claim 10, wherein:
the stirring oil and surfactant phase includes one of a single-surfactant system and a multi-surfactant system.

13. The nanoemulsion according to claim 10, further including:
a weight ratio of said oil and surfactant phase to said aqueous phase from 1:99 to 40:60.

14. The nanoemulsion according to claim 10, further including:
a weight ratio of said surfactant to said oil of the oil and surfactant phase from 10:1 to 1:10.

15. The nanoemulsion according to claim 1, wherein the cream is formed by:
preparing the phase 1 by mixing the purified water of 135 g, the methyparaben of 0.4 g, the glycerin of 3 g and the phenoxyethanol of 6.0 g in a beaker at the temperature of 70° C.;
preparing the phase by heating and mixing the mineral oil of 5 g, the avocado oil of 5 g, the isopropyl myristate of 5 g, the white petrolatum of 4 g, the vitamin E of 4.6 g, the emulsifying wax of 18 g, the bees wax of 7 g, the cetearyl alcohol of 3 g, the ethylhexylglycerin of 2 g and the propylparaben to the temperature of 70° C. in the separate container;
and transferring the mixture from the phase 2 at the temperature of 70° C. into the phase 1 mixing at the temperature of 70° C. with stirring, and cooling to room temperature, thereby forming the cream having a total weight of 200 grams.

* * * * *